(12) United States Patent
Muramatsu (10) Patent No.: US 8,173,378 B2
(45) Date of Patent: May 8, 2012

(54) METHODS OF USING AN ALPHA-1-ADRENERGIC RECEPTOR HAVING ALTERED LIGAND AFFINITY

(75) Inventor: Ikunobu Muramatsu, Fukui (JP)

(73) Assignees: Pharmacome LLC, Fukui (JP); Nippon Chemiphar Co., Ltd., Tokyo (JP)

( * ) Notice: Subject to any disclaimer, the term of this patent is extended or adjusted under 35 U.S.C. 154(b) by 0 days.

(21) Appl. No.: 12/451,558

(22) PCT Filed: May 22, 2008

(86) PCT No.: PCT/JP2008/059459
§ 371 (c)(1),
(2), (4) Date: Nov. 18, 2009

(87) PCT Pub. No.: WO2008/146707
PCT Pub. Date: Dec. 4, 2008

(65) Prior Publication Data
US 2010/0120068 A1    May 13, 2010

(30) Foreign Application Priority Data

May 23, 2007 (JP) ................................ 2007-137275

(51) Int. Cl.
*G01N 33/53* (2006.01)
*C12P 21/06* (2006.01)
*C12N 1/20* (2006.01)
*C12N 15/74* (2006.01)

(52) U.S. Cl. ..................... 435/7.2; 435/69.1; 435/252.3; 435/471

(58) Field of Classification Search .................. None
See application file for complete search history.

(56) References Cited

OTHER PUBLICATIONS

Fu Mlx et al. Clin. Exp. Immunol. 97:146-151, 1994.*
Ehlert FJ, et al. Life Sciences 64(6/7):387-394, 1999.*
Mironneau J, et al. Cellular Signalling 7(5):471-479, 1995.*
Christ T, et al. J. Mol. Cell. Cardioo. 41:716-723, 2006.*
"Identification of $\alpha$-1L Adrenoceptor in Rabbit Ear Artery" Y. Hiraizumi-Hiraoka et al., J. Pharmacology and Experimental Therapeutics 310:pp. 995-1002 (2004).
"Identification of $\alpha_{1L}$-Adrenoceptors in Eye and Blood Vessels" I. Muramatsu et al., Japanese Journal of Ocular Pharmacology, 19(1):pp. 49-51 (2005).
"$\alpha_1$-Adrenoceptor Subtypes and $\alpha1$-Adrenoceptor Antagonists" I. Muramatsu et al., Yakugaku Zasshi, 126: pp. 187-198 (2006).
"Variations in $\alpha_1$ Adrenoceptor and Supersensitivity" I. Muramatsu et al., Oyo Yakuri Jul. 30, 2004, vol. 66, No. 3/4, pp. 31-34.
"Pharmacological subclassification of $\alpha_1$-adrenoceptors in vascular smooth muscle" I. Muramatsu et al, Br. J. Pharmacol., 99:pp. 197-201 (1990).
"Functional Subclassification of Vascular $\alpha1$-adrenoreceptors" I. Muramatsu et al., Pharmacol. Communications 6: pp. 23-28 (1995).

"Identification of $\alpha$-1L and $\alpha$-1A Adrenoceptors in Human Prostate by Tissue Segment Binding" S. Morishima et al., Journal of Urology 177: pp. 377-381 (2007).
"Fundamental considerations of $\beta$-adrenoreceptor subtypes in human heart failure" P. Molenaar et al., TRENDS in Pharmacological Sciences 26:pp. 368-375 (2005).
""Breakthrough" Dopamine Supersensitivity during Ongoing Antipsychotic Treatment Leads to Treatment Failure over Time" A.N. Samaha et al., Journal of Neuroscience 27:pp. 2979-2986 (2007).
"RS-17053 (N-[2-(2-Cyclopropylmethoxyphenoxy)ethyl]-5-chloro-$\alpha$, $\alpha$ dimethyl-1$H$-indole-3-ethanamine hydrochloride), a Selective $\alpha_{1A}$-Adrenoceptor Antagonist, Displays Low Affinity for Functional $\alpha_1$-Adrenoceptors in Human Prostate: Implications for Adrenoceptor Classification" A.P.D.W. Ford et al., Molecular Pharmacology 49:pp. 209-215 (1996).
"Tissue Selectivity of KMD-3213, An $\alpha_1$-Adrenoceptor Antagonist, in Human Prostate and Vasculature" S. Murata et al., Journal of Urology 164:pp. 578-583 (2000).
"Pharmacological anaylsis of the novel, selective $\alpha1$-adrenoceptor antagonist, KMD-3213, and its suitability as a tritiated radioligand" S. Murata et al., British Journal of Pharmacology 127,:pp. 19-26 (1999).
"Identification, genomic organization and mRNA expression of CRELD1, the founding member of a unique family of matricellular proteins" P.A. Rupp et al., GENE 293:pp. 47-57 (2002).
"Missense Mutations in CRELD1 Are Associated with Cardiac Atrioventricular Septal Defects" S.W. Robinson et al., Am. J. Hum. Genet. 72:pp. 1047-1052 (2003).
Xu Jianguo et al: "Heterodimerization of $\alpha_{2A}$- and $\beta_1$-Adrenergic Receptors" Journal of Biological Chemistry, American Society for Biochemistry and Molecular Biology, Inc., vol. 278, No. 12, Mar. 21, 2003, pp. 10770-10777.
Li M. et al: "Modulation of Dopamine $D_2$ Receptor Signaling by Actin-Binding Protein (ABP-280)" Molecular Pharmacology, American Society for Pharmacology and Experimental Therapeutics, vol. 57, No. 3, Mar. 1, 2000, pp. 446-452.
McLatchie L.M. et al: "RAMPs Regulate the Transport and Ligand Specificity of the Calcitonin-Receptor-Like-Receptor" Nature, Nature Publishing Group, vol. 393, May 28, 1998, pp. 333-339.
Ford Anthony P.D.W. et al: "Pharmacological pleiotropism of the human recombinant $\alpha_{1A}$—adrenoceptor: implications for $\alpha_1$—adrenoceptor classification" British Journal of Pharmacology, vol. 121, No. 6, 1997, pp. 1127-1135.
Foerster Katharina et al: "Cardioprotection specific for the G protein $G_{i2}$ in chronic adrenergic signaling through $\beta_2$—adrenoceptors" Proceedings of the National Academy of Sciences of the United States of America, vol. 100, No. 24, Nov. 25, 2003, pp. 14475-14480.
European Search Report regarding European Application No. 08753090.3 and EPO Form 1703, mailed on Sep. 28, 2010.

* cited by examiner

*Primary Examiner* — Robert Landsman
(74) *Attorney, Agent, or Firm* — Edwards Wildman Palmer LLP; David G. Conlin; Kathryn A. Piffat, Esq.

(57) ABSTRACT

A modified G-protein-coupled receptor (GPCR), having modified ligand affinity is provided by binding a G-protein-coupled receptor to a polypeptide consisting of an amino acid sequence of SEQ ID NO: 1. Furthermore, agonists for or antagonists against the modified GPCR are screened using a transformant in which the modified GPCR has been expressed. This makes it possible to provide a technique for analyzing the function of many putative GPCRs whose entities have not been clarified.

4 Claims, 2 Drawing Sheets

SEQUENCE LISTING

```
<160> NUMBER OF SEQ ID NOS: 6

<210> SEQ ID NO 1
<211> LENGTH: 420
<212> TYPE: PRT
<213> ORGANISM: human

<400> SEQUENCE: 1

Met Ala Pro Trp Pro Pro Lys Gly Leu Val Pro Ala Val Leu Trp Gly
 1               5                  10                  15

Leu Ser Leu Phe Leu Asn Leu Pro Gly Pro Ile Trp Leu Gln Pro Ser
                20                  25                  30

Pro Pro Pro Gln Ser Ser Pro Pro Gln Pro His Pro Cys His Thr
            35                  40                  45

Cys Arg Gly Leu Val Asp Ser Phe Asn Lys Gly Leu Glu Arg Thr Ile
 50                  55                  60

Arg Asp Asn Phe Gly Gly Gly Asn Thr Ala Trp Glu Glu Glu Asn Leu
 65                  70                  75                  80

Ser Lys Tyr Lys Asp Ser Glu Thr Arg Leu Val Glu Val Leu Glu Gly
                85                  90                  95

Val Cys Ser Lys Ser Asp Phe Glu Cys His Arg Leu Leu Glu Leu Ser
               100                 105                 110

Glu Glu Leu Val Glu Ser Trp Trp Phe His Lys Gln Gln Glu Ala Pro
           115                 120                 125

Asp Leu Phe Gln Trp Leu Cys Ser Asp Ser Leu Lys Leu Cys Cys Pro
       130                 135                 140

Ala Gly Thr Phe Gly Pro Ser Cys Leu Pro Cys Pro Gly Gly Thr Glu
145                 150                 155                 160

Arg Pro Cys Gly Gly Tyr Gly Gln Cys Glu Gly Glu Gly Thr Arg Gly
               165                 170                 175

Gly Ser Gly His Cys Asp Cys Gln Ala Gly Tyr Gly Gly Glu Ala Cys
           180                 185                 190

Gly Gln Cys Gly Leu Gly Tyr Phe Glu Ala Glu Arg Asn Ala Ser His
       195                 200                 205
```

-continued

| Leu | Val | Cys | Ser | Ala | Cys | Phe | Gly | Pro | Cys | Ala | Arg | Cys | Ser | Gly | Pro |
| | | | 210 | | | | 215 | | | | 220 | | | | |

| Glu | Glu | Ser | Asn | Cys | Leu | Gln | Cys | Lys | Lys | Gly | Trp | Ala | Leu | His | His |
| 225 | | | | | 230 | | | | | 235 | | | | | 240 |

Leu Lys Cys Val Asp Ile Asp Glu Cys Gly Thr Glu Gly Ala Asn Cys
                  245                  250                  255

Gly Ala Asp Gln Phe Cys Val Asn Thr Glu Gly Ser Tyr Glu Cys Arg
                260                  265                  270

Asp Cys Ala Lys Ala Cys Leu Gly Cys Met Gly Ala Gly Pro Gly Arg
        275                  280                  285

Cys Lys Lys Cys Ser Pro Gly Tyr Gln Gln Val Gly Ser Lys Cys Leu
        290                  295                  300

Asp Val Asp Glu Cys Glu Thr Glu Val Cys Pro Gly Glu Asn Lys Gln
305                  310                  315                  320

Cys Glu Asn Thr Glu Gly Gly Tyr Arg Cys Ile Cys Ala Glu Gly Tyr
                325                  330                  335

Lys Gln Met Glu Gly Ile Cys Val Lys Glu Gln Ile Pro Glu Ser Ala
                340                  345                  350

Gly Phe Phe Ser Glu Met Thr Glu Asp Glu Leu Val Val Leu Gln Gln
        355                  360                  365

Met Phe Phe Gly Ile Ile Ile Cys Ala Leu Ala Thr Leu Ala Ala Lys
        370                  375                  380

Gly Asp Leu Val Phe Thr Ala Ile Phe Ile Gly Ala Val Ala Ala Met
385                  390                  395                  400

Thr Gly Tyr Trp Leu Ser Glu Arg Ser Asp Arg Val Leu Glu Gly Phe
                405                  410                  415

Ile Lys Gly Arg
        420

<210> SEQ ID NO 2
<211> LENGTH: 2723
<212> TYPE: DNA
<213> ORGANISM: human

<400> SEQUENCE: 2

```
tgcgttttac gcaggctgtg cagcgacgc ggtgaggaga cggcccacgg cgcccgcggg      60
ctggggcggt cgcttcttcc ttctccgtgg cctacgaggg tctggatcct tctctgccgg     120
ctcgtgggcc gtgcctttgc ccttctgcga ggccctgaat ctgatccctt cccttcatat     180
ccggatccgg gctcctccct ccaagcccgg ggttccggac acctccccca agacaacccc     240
tctggcctcc tctccttcag tacttggaat ctgatctctt ctccctaatt ctgcggatcc     300
ggcccctaat attctttatc agaccctcag acaagaggct gacttctgcc cccttgtcaa     360
ggagcgaggc cactttcctc tccaccccat gctagcgagg ataacttatt tctcttctgg     420
aattgcatct tatgcgcctt tccccaccca tccccacagc ccctgcaata cccagtttgg     480
cctcttttgc ttgtaataac gcagatccca gcgccacggc accttagaac agacctttt      540 ctttctcgcg tggggcctga ctccttcagt gaagcctctc cacgccctct atctgcaggt     600
ccccagcctg ggtaaagatg gcccatggc cccgaaggg cctagtccca gctgtgctct     660
ggggcctcag cctcttcctc aacctcccag gacctatctg gctccagccc tctccacctc     720
cccagtcttc tccccgcct cagcccatc cgtgtcatac ctgccgggga ctggttgaca     780
gctttaacaa gggcctggag agaaccatcc gggacaactt tggaggtgga aacactgcct     840
gggaggaaga gaatttgtcc aaatacaaag acagtgagac ccgcctggta gaggtgctgg     900
```

| | |
|---|---|
| agggtgtgtg cagcaagtca gacttcgagt gccaccgcct gctggagctg agtgaggagc | 960 |
| tggtggagag ctggtggttt cacaagcagc aggaggcccc ggacctcttc cagtggctgt | 1020 |
| gctcagattc cctgaagctc tgctgccccg caggcacctt cgggccctcc tgccttccct | 1080 |
| gtcctggggg aacagagagg ccctgcggtg gctacgggca gtgtgaagga aagggacac | 1140 |
| gagggggcag cgggcactgt gactgccaag ccggctacgg gggtgaggcc tgtggccagt | 1200 |
| gtggccttgg ctactttgag gcagaacgca acgccagcca tctggtatgt tcggcttgtt | 1260 |
| ttggcccctg tgcccgatgc tcaggacctg aggaatcaaa ctgtttgcaa tgcaagaagg | 1320 |
| gctgggccct gcatcacctc aagtgtgtag acattgatga gtgtggcaca gagggagcca | 1380 |
| actgtggagc tgaccaattc tgcgtgaaca ctgagggctc ctatgagtgc cgagactgtg | 1440 |
| ccaaggcctg cctaggctgc atgggggcag ggccaggtcg ctgtaagaag tgtagccctg | 1500 |
| gctatcagca ggtgggctcc aagtgtctcg atgtggatga gtgtgagaca gaggtgtgtc | 1560 |
| cgggagagaa caagcagtgt gaaaacaccg agggcggtta tcgctgcatc tgtgccgagg | 1620 |
| gctacaagca gatggaaggc atctgtgtga aggagcagat cccagagtca gcaggcttct | 1680 |
| tctcagagat gacagaagac gagttggtgg tgctgcagca gatgttcttt ggcatcatca | 1740 |
| tctgtgcact ggccacgctg gctgctaagg gcgacttggt gttcaccgcc atcttcattg | 1800 |
| gggctgtggc ggccatgact ggctactggt tgtcagagcg cagtgaccgt gtgctggagg | 1860 |
| gcttcatcaa gggcagataa tcgcggccac cacctgtagg acctcctccc acccacgctg | 1920 |
| cccccagagc ttgggctgcc ctcctgctgg acactcagga cagcttggtt tattttgag | 1980 |
| agtggggtaa gcaccctac ctgccttaca gagcagccca ggtacccagg cccgggcaga | 2040 |
| caaggcccct gggtaaaaa gtagccctga aggtggatac catgagctct tcacctggcg | 2100 |
| gggactggca ggcttcacaa tgtgtgaatt tcaaaagttt ttccttaatg gtggctgcta | 2160 |
| gagctttggc ccctgcttag gattaggtgg tcctcacagg ggtggggcca tcacagctcc | 2220 |
| ctcctgccag ctgcatgctg ccagttcctg ttctgtgttc accacatccc cacaccccat | 2280 |
| tgccacttat ttattcatct caggaaataa agaaaggtct tggaaagtta aaaggcatca | 2340 |
| gtcttactac ctgtcccacc acccccacct tagggaaatg tcctagaatc ctgggaaatt | 2400 |
| gagggcttct ttgatggtga gtggagaaaa gatagaggag aaggttgccc ctgaagtgct | 2460 |
| gttaggagaa ggaggataga ggaatcagcc ttaggagggt tccatgccag ctgtcatttg | 2520 |
| gcaaaggacc ctgacagat gacttttgcc tctgaacttc actcttctct ttcctcaaat | 2580 |
| gggcttcata atgctttcca ctcaggctta acatgagaat taaatgaggt gacaaatgtg | 2640 |
| aagacctgga cagtacacaa cagatattca ataaaagtgt ggtcgccatt atgaccagag | 2700 |
| cctccaaaaa aaaaaaaaaa aaa | 2723 |

<210> SEQ ID NO 3
<211> LENGTH: 466
<212> TYPE: PRT
<213> ORGANISM: human

<400> SEQUENCE: 3

Met Val Phe Leu Ser Gly Asn Ala Ser Asp Ser Ser Asn Cys Thr Gln
1               5                   10                  15

Pro Pro Ala Pro Val Asn Ile Ser Lys Ala Ile Leu Leu Gly Val Ile
                20                  25                  30

Leu Gly Gly Leu Ile Leu Phe Gly Val Leu Gly Asn Ile Leu Val Ile
            35                  40                  45

```
Leu Ser Val Ala Cys His Arg His Leu His Ser Val Thr His Tyr Tyr
    50                  55                  60

Ile Val Asn Leu Ala Val Ala Asp Leu Leu Leu Thr Ser Thr Val Leu
65                  70                  75                  80

Pro Phe Ser Ala Ile Phe Glu Val Leu Gly Tyr Trp Ala Phe Gly Arg
                85                  90                  95

Val Phe Cys Asn Ile Trp Ala Ala Val Asp Val Leu Cys Cys Thr Ala
            100                 105                 110

Ser Ile Met Gly Leu Cys Ile Ile Ser Ile Asp Arg Tyr Ile Gly Val
        115                 120                 125

Ser Tyr Pro Leu Arg Tyr Pro Thr Ile Val Thr Gln Arg Arg Gly Leu
    130                 135                 140

Met Ala Leu Leu Cys Val Trp Ala Leu Ser Leu Val Ile Ser Ile Gly
145                 150                 155                 160

Pro Leu Phe Gly Trp Arg Gln Pro Ala Pro Glu Asp Glu Thr Ile Cys
                165                 170                 175

Gln Ile Asn Glu Glu Pro Gly Tyr Val Leu Phe Ser Ala Leu Gly Ser
            180                 185                 190

Phe Tyr Leu Pro Leu Ala Ile Ile Leu Val Met Tyr Cys Arg Val Tyr
    195                 200                 205

Val Val Ala Lys Arg Glu Ser Arg Gly Leu Lys Ser Gly Leu Lys Thr
210                 215                 220

Asp Lys Ser Asp Ser Glu Gln Val Thr Leu Arg Ile His Arg Lys Asn
225                 230                 235                 240

Ala Pro Ala Gly Gly Ser Gly Met Ala Ser Ala Lys Thr Lys Thr His
                245                 250                 255

Phe Ser Val Arg Leu Leu Lys Phe Ser Arg Glu Lys Lys Ala Ala Lys
            260                 265                 270

Thr Leu Gly Ile Val Val Gly Cys Phe Val Leu Cys Trp Leu Pro Phe
        275                 280                 285

Phe Leu Val Met Pro Ile Gly Ser Phe Phe Pro Asp Phe Lys Pro Ser
    290                 295                 300

Glu Thr Val Phe Lys Ile Val Phe Trp Leu Gly Tyr Leu Asn Ser Cys
305                 310                 315                 320

Ile Asn Pro Ile Ile Tyr Pro Cys Ser Ser Gln Glu Phe Lys Lys Ala
                325                 330                 335

Phe Gln Asn Val Leu Arg Ile Gln Cys Leu Cys Arg Lys Gln Ser Ser
            340                 345                 350

Lys His Ala Leu Gly Tyr Thr Leu His Pro Pro Ser Gln Ala Val Glu
        355                 360                 365

Gly Gln His Lys Asp Met Val Arg Ile Pro Val Gly Ser Arg Glu Thr
    370                 375                 380

Phe Tyr Arg Ile Ser Lys Thr Asp Gly Val Cys Glu Trp Lys Phe Phe
385                 390                 395                 400

Ser Ser Met Pro Arg Gly Ser Ala Arg Ile Thr Val Ser Lys Asp Gln
                405                 410                 415

Ser Ser Cys Thr Thr Ala Arg Val Arg Ser Lys Ser Phe Leu Gln Val
            420                 425                 430

Cys Cys Cys Val Gly Pro Ser Thr Pro Ser Leu Asp Lys Asn His Gln
        435                 440                 445

Val Pro Thr Ile Lys Val His Thr Ile Ser Leu Ser Glu Asn Gly Glu
    450                 455                 460

Glu Val
465
```

```
<210> SEQ ID NO 4
<211> LENGTH: 1500
<212> TYPE: DNA
<213> ORGANISM: human

<400> SEQUENCE: 4
ccgcctccgc gccagcccgg gaggtggccc tgacagccgg acctcgcccg gccccggctg      60
ggaccatggt gtttctctcg ggaaatgctt ccgacagctc caactgcacc caaccgccgg     120
caccggtgaa catttccaag gccattctgc tcggggtgat cttgggggc ctcattcttt      180 tcggggtgct gggtaacatc ctagtgatcc tctccgtagc ctgtcaccga cacctgcact     240
cagtcacgca ctactacatc gtcaacctgg cggtggccga cctcctgctc acctccacgg     300
tgctgccctt ctccgccatc ttcgaggtcc taggctactg ggcctccggc agggtcttct     360
gcaacatctg ggcggcagtg gatgtgctgt gctgcaccgc gtccatcatg ggcctctgca     420
tcatctccat cgaccgctac atcggcgtga gctaccgct gcgctaccca accatcgtca      480
cccagaggag gggtctcatg gctctgctct gcgtctgggc actctccctg gtcatatcca     540 ttggaccct gttcggctgg aggcagccgg ccccgagga cgagaccatc tgccagatca      600
acgaggagcc gggctacgtg ctcttctcag cgctgggctc cttctacctg cctctggcca     660
tcatcctggt catgtactgc cgcgtctacg tggtggccaa gagggagagc cggggcctca     720
agtctggcct caagaccgac aagtcggact cggagcaagt gacgctccgc atccatcgga     780
aaaacgcccc ggcaggaggc agcgggatgg ccagcgccaa gaccaagacg cacttctcag     840
tgaggctcct caagttctcc cgggagaaga aagcggccaa aacgctgggc atcgtggtcg     900
gctgcttcgt cctctgctgg ctgccttttt tcttagtcat gcccattggg tctttcttcc     960
ctgatttcaa gcccctctgaa acagttttta aaatagtatt ttggctcgga tatctaaaca    1020
gctgcatcaa ccccatcata tacccatgct ccagccaaga gttcaaaaag gcctttcaga    1080
atgtcttgag aatccagtgt ctctgcagaa agcagtcttc caaacatgcc ctgggctaca    1140
ccctgcaccc gccccagccag gccgtggaag ggcaacacaa ggacatggtg cgcatccccg    1200
tgggatcaag agagaccttc tacaggatct ccaagacgga tggcgtttgt gaatggaaat    1260
ttttctcttc catgccccgt ggatctgcca ggattacagt gtccaaagac caatcctcct    1320
gtaccacagc ccgggtgaga agtaaaagct ttttgcaggt ctgctgctgt gtagggccct    1380
caacccccag ccttgacaag aaccatcaag ttccaaccat taaggtccac accatctccc    1440
tcagtgagaa cggggaggaa gtctaggaca ggaaagatgc agaggaaagg ggaatatctt    1500

<210> SEQ ID NO 5
<211> LENGTH: 55
<212> TYPE: DNA
<213> ORGANISM: Artificial Sequence
<220> FEATURE:
<223> OTHER INFORMATION: Description of Artificial Sequence: Synthesized
      Oligo Nucleotide

<400> SEQUENCE: 5
gatccaggcg acttagtgtt caccttcaag agaggtgaac actaagtcgc cttta          55

<210> SEQ ID NO 6
<211> LENGTH: 55
<212> TYPE: DNA
<213> ORGANISM: Artificial Sequence
<220> FEATURE:
<223> OTHER INFORMATION: Description of Artificial Sequence: Synthesized
      Oligo Nucleotide
```

-continued

```
<400> SEQUENCE: 6
agcttaaagg cgacttagtg ttcacctctc ttgaaggtga acactaagtc gcctg      55
```

METHODS OF USING AN ALPHA-1-ADRENERGIC RECEPTOR HAVING ALTERED LIGAND AFFINITY

CROSS-REFERENCES TO RELATED APPLICATIONS

The present application is the 35 U.S.C. §371 national stage of PCT application PCT/JP2008/059459, filed May 22, 2008, which claims benefit of Japanese Application 2007-137275, filed May 23, 2007, the disclosures of all of which are incorporated herein by reference.

TECHNICAL FIELD

The present invention relates to G-protein-coupled receptors (GPCRs) having modified ligand affinity and use thereof and, more particularly, the present invention relates to a GPCR having ligand affinity modified by forming a complex with a particular protein and use thereof.

BACKGROUND ART

Many reactions in living organisms are caused by entrance of extracellular information into cells and by propagation of the information in the cells. Membrane receptors serve as mediators through which extracellular information is transmitted into cells. Among them, GPCRs having seven transmembrane domains is well known as a major category of membrane receptors.

When a ligand (such as amino acids, peptides or amines) binds to a GPCR, the GPCR transmits its information into a cell via a trimeric G protein. G proteins coupled to GPCRs are classified into Gs, Gi, Gq, and the like, which activate/inactivate different effector pathways (e.g., cAMP pathway, cGMP pathway, and phospholipase C pathway), respectively. For example, $\alpha_1$-adrenergic receptor is mainly coupled to Gq protein to promote phospholipase C system, which produces diacylglycerol and inositol trisphosphate, thus increasing intracellular $Ca^{2+}$. $\alpha_2$-adrenergic receptor is mainly coupled to Gi protein to suppress adenylate cyclase system, thus decreasing cAMP. Further, β-adrenergic receptor is mainly coupled to Gs protein to promote adenylate cyclase system, which thus increases cAMP.

GPCRs widely occur and function in our body. For example, $\alpha_1$-adrenergic receptors exist peripherally in blood vessel, prostate, and produce the contractions. Further, $\alpha_1$-adrenergic receptors are known to function in central nervous system. β-adrenergic receptors in heart and fat tissue play important roles in heart rate and lipolysis.

GPCRs and their signal transduction systems are known not only to control the physiological homeostasis in our body but also to be involved in pathophysiological status of various diseases. Therefore, in order to treat the diseases it will be very significant to identify the GPCRs which are related to the diseases and then to develop their specific drugs (such as agonists or antagonists).

Non Patent Literature 1
Muramatsu, I. et al. Br. *J. Pharmacol.*, 99: 197 (1990)
Non Patent Literature 2
Muramatsu, I. et al. *Pharmacol. Commun.*, 6: 23 (1995)
Non Patent Literature 3
Morishima, S. et al. *J. Urol.* 177: 377-381 (2007)
Non Patent Literature 4
Molenaar, P. and Parsonage, W. A. *Trends Pharmacol. Sci.*, 26: 368-375 (2005)
Non Patent Literature 5
Samaha, A. N. et al., *J. Neurosci.* 27: 2979-2986 (2007)

SUMMARY OF INVENTION

There has been significant progress in GPCR research, whereby a large number of GPCRs have been identified. However, there still exist several putative GPCRs whose phenotypes are identified but whose entities are yet unknown. For example, $\alpha_1$-adrenergic receptors are now classified into three subtypes ($\alpha_{1A}$, $\alpha_{1B}$ and $\alpha_{1D}$) based on their distinct genes. However, in addition to the classical $\alpha_1$-adrenergic receptors, the presence of an additional subtype ($\alpha_{1L}$) which shows different pharmacological profile (phenotype) from the classical subtypes has been proposed. The $\alpha_{1L}$-subtype has significantly lower affinity for a representative $\alpha_1$ blocker (prazosin) than $\alpha_{1A}$-, $\alpha_{1B}$- and $\alpha_{1D}$-subtypes, The $\alpha_{1L}$-subtype can be detected only in intact strips or segments of native tissues but not be identified in their tissue homogenates (see Non Patent Literatures 1 to 3). Further, subtypes of $\beta_1$ adrenaline receptor $\beta_{1H}$ and $\beta_{1L}$) that differ in phenotype are known to be expressed from the same genes (see Non Patent Literature 4). Such subtype only has its phenotype known, and has its entity unknown. The similar cases may be also pointed out for dopamine receptors, muscarinic receptors, or endothelin receptors (see Non Patent Literature 5 and the like). However, the underlying mechanisms for different phenotype formation of the same gene product have not yet known.

The present invention has been made in view of this problem, and it is an object of the present invention to provide a technique for analyzing the function of a G-protein-coupled receptor whose entity has not been clarified.

A protein complex according to the present invention is characterized by binding of a GPCR to (1) a polypeptide consisting of an amino-acid sequence of SEQ ID NO: 1; (2) a polypeptide (i) consisting of an amino-acid sequence of SEQ ID NO: 1 with a deletion, insertion, substitution, or addition of one or several amino acids, and (ii) having activity to modify ligand affinity of a GPCR with which the polypeptide has formed a complex; (3) a polypeptide encoded by a polynucleotide consisting of a nucleotide sequence of SEQ ID NO: 2; (4) a polypeptide (i) encoded by a polynucleotide consisting of a nucleotide sequence of SEQ ID. NO: 2 with a deletion, insertion, substitution, or addition of one or several nucleotides, and (ii) having activity to modify ligand affinity of a GPCR with which the polypeptide has formed a complex; (5) a polypeptide (i) encoded by polynucleotide capable of hybridizing under stringent conditions with a polynucleotide consisting of a sequence complementary to a nucleotide sequence of SEQ ID NO: 2 and (ii) having activity to modify ligand affinity of a GPCR with which the polypeptide has formed a complex; or (6) a polypeptide (i) coded for by a polynucleotide having a sequence identity of 70% or higher with a polynucleotide consisting of a nucleotide sequence of SEQ ID NO: 2 and (ii) having activity to modify ligand affinity of a GPCR with which the polypeptide has formed a complex.

A method according to the present invention for producing a protein complex is characterized by including the step of causing a GPCR and a polypeptide to coexist on a lipid membrane, the polypeptide being (1) a polypeptide consisting of an amino-acid sequence of SEQ ID NO: 1; (2) a polypeptide (i) consisting of an amino-acid sequence of SEQ ID NO: 1 with a deletion, insertion, substitution, or addition of one or several amino acids, and (ii) having activity to modify ligand affinity of a GPCR with which the polypeptide has formed a complex; (3) a polypeptide encoded by a polynucleotide consisting of a nucleotide sequence of SEQ ID NO: 2; (4) a polypeptide (i) encoded by a polynucleotide consisting of a nucleotide sequence of SEQ ID NO: 2 with a deletion, insertion, substitution, or addition of one or several nucleotides, and (ii) having activity to modify ligand affinity of a GPCR with which the polypeptide has formed a complex; (5) a polypeptide (i) encoded by a polynucleotide capable of hybridizing under stringent conditions with a polynucleotide consisting of a sequence complementary to a nucleotide sequence of SEQ ID NO: 2 and (ii) having activity to modify ligand affinity of a GPCR with which the polypeptide has formed a complex; or (6) a polypeptide (i) coded for by a polynucleotide having a sequence identity of 70% or higher with a polynucleotide consisting of a nucleotide sequence of SEQ ID NO: 2 and (ii) having activity to modify ligand affinity of a GPCR with which the polypeptide has formed a complex.

With this feature, the present invention can modify the ligand affinity of a GPCR. That is, the method according to the present invention for producing a protein complex can also be a method for modifying the affinity of a GPCR for its ligands.

A lipid membrane according to the present invention is characterized by containing the protein complex. A method according to the present invention for producing the lipid membrane is characterized by including the step of causing a GPCR and a polypeptide to coexist on the lipid membrane, the polypeptide being (1) a polypeptide consisting of an amino-acid sequence of SEQ ID NO: 1; (2) a polypeptide (i) consisting of an amino-acid sequence of SEQ ID NO: 1 with a deletion, insertion, substitution, or addition of one or several amino acids, and (ii) having activity to modify ligand affinity of a G-protein-coupled receptor with which the polypeptide has formed a complex; (3) a polypeptide encoded by a polynucleotide consisting of a nucleotide sequence of SEQ ID NO: 2; (4) a polypeptide (i) encoded by a polynucleotide consisting of a nucleotide sequence of SEQ ID NO: 2 with a deletion, insertion, substitution, or addition of one or several nucleotides, and (ii) having activity to modify ligand affinity of a GPCR with which the polypeptide has formed a complex; (5) a polypeptide (i) encoded by a polynucleotide capable of hybridizing under stringent conditions with a polynucleotide consisting of a sequence complementary to a nucleotide sequence of SEQ ID NO: 2 and (ii) having activity to modify ligand affinity of a GPCR with which the polypeptide has formed a complex; or (6) a polypeptide (i) coded for by a polynucleotide having a sequence identity of 70% or higher with a polynucleotide consisting of a nucleotide sequence of SEQ ID NO: 2 and (ii) having activity to modify ligand affinity of a GPCR with which the polypeptide has formed a complex.

Furthermore, a transformant according to the present invention is characterized by containing the protein complex. A method according to the present invention for producing the transformant is characterized by including the step of expressing the protein complex, and preferably includes the step of introducing, into a cell, a gene encoding a GPCR and a gene encoding the polypeptide.

With this feature, the present invention makes it easy to analyze the function of a GPCR having modified ligand affinity.

A method according to the present invention for screening agonists or antagonists of a GPCR having modified ligand affinity is characterized by including the steps of: [I] generating a protein complex by causing a GPCR and a polypeptide to coexist on a lipid membrane; and [II] incubating the protein complex together with a candidate factor, the polypeptide being (1) a polypeptide consisting of an amino-acid sequence of SEQ ID NO: 1; (2) a polypeptide (i) consisting of an amino-acid sequence of SEQ ID NO: 1 with a deletion, insertion, substitution, or addition of one or several amino acids, and (ii) having activity to modify ligand affinity of a GPCR with which the polypeptide has formed a complex; (3) a polypeptide encoded by a polynucleotide consisting of a nucleotide sequence of SEQ ID NO: 2; (4) a polypeptide (i) encoded by a polynucleotide consisting of a nucleotide sequence of SEQ ID NO: 2 with a deletion, insertion, substitution, or addition of one or several nucleotides, and (ii) having activity to modify ligand affinity of a GPCR with which the polypeptide has formed a complex; (5) a polypeptide (i) encoded by a polynucleotide capable of hybridizing under stringent conditions with a polynucleotide consisting of a sequence complementary to a nucleotide sequence of SEQ ID NO: 2 and (ii) having activity to modify ligand affinity of a GPCR with which the polypeptide has formed a complex; or (6) a polypeptide (i) coded for by a polynucleotide having a sequence identity of 70% or higher with a polynucleotide consisting of a nucleotide sequence of SEQ ID NO: 2 and (ii) having activity to modify ligand affinity of a GPCR with which the polypeptide has formed a complex.

A method according to the present invention for producing a transformant expressing a GPCR having modified ligand affinity is characterized by including the step of inhibiting expression of a polypeptide in the cell in which a GPCR has been expressed, the polypeptide being (1) a polypeptide consisting of an amino-acid sequence of SEQ ID NO: 1; (2) a polypeptide (i) consisting of an amino-acid sequence of SEQ ID NO: 1 with a deletion, insertion, substitution, or addition of one or several amino acids, and (ii) having activity to modify ligand affinity of a GPCR with which the polypeptide has formed a complex; (3) a polypeptide encoded by a polynucleotide consisting of a nucleotide sequence of SEQ ID NO: 2; (4) a polypeptide (i) encoded by a polynucleotide consisting of a nucleotide sequence of SEQ ID NO: 2 with a deletion, insertion, substitution, or addition of one or several nucleotides, and (ii) having activity to modify ligand affinity of a GPCR with which the polypeptide has formed a complex; (5) a polypeptide (i) encoded by a polynucleotide capable of hybridizing under stringent conditions with a polynucleotide consisting of a sequence complementary to a nucleotide sequence of SEQ ID NO: 2 and (ii) having activity to modify ligand affinity of a GPCR with which the polypeptide has formed a complex; or (6) a polypeptide (i) coded for by a polynucleotide having a sequence identity of 70% or higher with a polynucleotide consisting of a nucleotide sequence of SEQ ID NO: 2 and (ii) having activity to modify ligand affinity of a GPCR with which the polypeptide has formed a complex.

With this feature, the present invention makes it easy to analyze the function of a GPCR having modified ligand affinity, and can modify the ligand affinity of a GPCR. That is, the present invention can also be a method for modifying the affinity of a GPCR for its ligands.

The producing method according to the present invention is preferably such that the polypeptide is an endogenous protein, and that the step of inhibiting the expression of the polypeptide is performed according to an RNAi method. Further, the cell may be a transformant expressing an exogenous GPCR.

A method according to the present invention for screening agonists or antagonists of a GPCR having modified ligand affinity is characterized by including the steps of: [I] inhibiting expression of a polypeptide in the cell in which a GPCR has been expressed; and [II] incubating the cell together with a candidate factor, the polypeptide being (1) a polypeptide consisting of an amino-acid sequence of SEQ ID NO: 1; (2) a polypeptide (i) consisting of an amino-acid sequence of SEQ ID NO: 1 with a deletion, insertion, substitution, or addition of one or several amino acids, and (ii) having activity to modify ligand affinity of a GPCR with which the polypeptide has formed a complex; (3) a polypeptide encoded by a polynucleotide consisting of a nucleotide sequence of SEQ ID NO: 2; (4) a polypeptide (i) encoded by a polynucleotide consisting of a nucleotide sequence of SEQ ID NO: 2 with a deletion, insertion, substitution, or addition of one or several nucleotides, and (ii) having activity to modify ligand affinity of a GPCR with which the polypeptide has formed a complex; (5) a polypeptide (i) encoded by a polynucleotide capable of hybridizing under stringent conditions with a polynucleotide consisting of a sequence complementary to a nucleotide sequence of SEQ ID NO: 2 and (ii) having activity to modify ligand affinity of a GPCR with which the polypeptide has formed a complex; or (6) a polypeptide (i) coded for by a polynucleotide having a sequence identity of 70% or higher with a polynucleotide consisting of a nucleotide sequence of SEQ ID NO: 2 and (ii) having activity to modify ligand affinity of a GPCR with which the polypeptide has formed a complex. It is preferable that the screening method according to the present invention further include the step of measuring an intracellular $Ca^{2+}$ concentration or the step of measuring metabolism of intracellular inositol phosphate.

In the present invention, it is preferable that the GPCR constituting the protein complex be an adrenergic receptor, a dopamine receptor, a muscarinic receptor, or an endothelin receptors, and the adrenergic receptors may be α-receptor or β-receptor. Further, it is preferable that the dopamine receptor be a D2 receptor. It is preferable that the α-receptor be an $α_1$-receptor, and it is more preferable that the $α_1$-receptor be an $α_{1A}$-subtype. In a preferred embodiment, a protein complex according to the present invention is $α_{1L}$-subtype or $β_{1L}$-subtype of adrenergic receptors.

For a fuller understanding of the nature and advantages of the invention, reference should be made to the ensuing detailed description taken in conjunction with the accompanying drawings.

BRIEF DESCRIPTION OF DRAWINGS

FIG. 1

FIGS. 2(a) and (b)

(a) of FIG. 2 shows competition-binding curves for prazosin in $α_{1L}$, cells and $α_{1A}$ cells (whole cell binding experiment). (b) of FIG. 2 shows competition-binding curves for prazosin in homogenates of $α_{1L}$ cells and $α_{1A}$ cells. Dashed line with closed squares: A competition-binding curve for prazosin in whole $α_{1L}$ cells was described for comparison against the curves in homogenates.

DESCRIPTION OF EMBODIMENTS

[1: Protein Complex]

The present invention provides a protein complex of a GPCR and a particular polypeptide. When used in the present specification, the term "complex" means an integrated combination of a plurality of substances, and "complex formation" and "integration" are used interchangeably. It should be noted that a plurality of substances forming a complex only need to interact with each other in close proximity and may or may not bind to each other. In a preferred embodiment, a protein complex according to the present invention is such a state that a GPCR and a particular polypeptide interact with each other in close proximity and, as a result, functions as a GPCR having modified ligand affinity.

The present specification describes the present invention by taking an adrenergic receptor (in particular, of $α_{1A}$-subtype) as an example of a GPCR whose ligand affinity is modified by interacting with a particular polypeptide. However, a person skilled in the art who has read the present specification would easily understand that a GPCR constituting the present invention is not limited to an adrenergic receptor. Further, a person skilled in the art could easily obtain information on the sequence of a GPCR constituting the present invention.

Adrenergic receptors are well known to mediate the functions of the autonomic nervous system (sympathetic nervous system). Binding of adrenaline, noradrenaline, or the like to the adrenergic receptor causes various physiological responses such as contractions of vascular smooth muscle, increases in blood pressure and heart rate, dilation of the pupil, and an increase in blood glucose level.

The progress in research and the development of a new variety of drugs have made clear that adrenergic receptors are classified into various types. In the past, adrenergic receptors were classified into α-receptor and β-receptor according to their difference in reactivity to drugs such as isoproterenol and phentolamine, and further classified into pharmacological subtypes ($α_1$-receptor, $α_2$-receptor, and β-receptor). These receptors are known to exhibit different distributions in each tissue and to play different functions. For example, the $α_1$-adrenergic receptors are known to play as an important mediator causing contractions of vascular smooth muscle, prostate, and the like, and also known to be involved in the regulation of consciousness and emotion in central nervous system.

Now that the mapping of the human genome has been finished, the structures and functions of many proteins can be shown on a genetic level. In $α_1$-adrenergic receptors, three subtypes ($α_{1A}$, $α_{1B}$, and $α_{1D}$) were identified according to their distinct genes. These classical subtypes are known to coincide well with pharmacologically identified subtypes. In this way, it may be considered that one receptor subtype is basically originated from one distinct gene.

However, it has been long pointed out that a unique $α_1$-adrenergic receptor occurs and functions in some tissues of our body. Because of its low affinity for a representative $α_1$ blocker (prazosin), the unique subtype has been called "$α_{1L}$-subtype", although the corresponding gene has not been yet cloned.

Table 1 shows the classification and drug selectivity of $α_1$-adrenergic receptors.

TABLE 1

Classification and Drug Selectivity of $α_1$-adrenergic Receptors

| | Affinity (pKb) | | | | |
|---|---|---|---|---|---|
| Subtypes | silodosin[1,3,4,5] | tamsulosin[1,3,4] | prazosin[1,2,3,4,5] | RS-17053[2,4] | BMY 7378[4,5] |
| α1A | 10.7-9.5 | 10.4-9.9 | 10.6-9.3 | 9.1-8.4 | 6.9-5.6 |
| α1L | 10.7-9.5 | 10.4-9.9 | 8.3-7.6 | 6.3 | 6.9-5.6 |
| α1B | 8.1 | 9.3 | 10.6-10.1 | 7.8 | 7.4 |
| α1D | 8.6 | 9.9 | 10.1-9.9 | 7.8 | 9.1 |

The effects of the compounds shown in Table 1 are based on the following literatures:
1. Muramatsu, I. et al. *Pharmacol. Commun.*, 6: 23 (1995)
2. Ford, A P. et al. *Mol. Pharmacol.*, 49: 209 (1996)
3. Murata, S. et al. *J. Urol.*, 164: 578 (2000)
4. Hiraizumi-Hiraoka, Y. et al. *J. Pharmacol. Exp. Ther.*, 310: 995 (2004)
5. Murata, S. et al. *Br. J. Pharmacol.*, 127: 19 (1999)

In bioassay studies, the $\alpha_{1L}$-subtype has been clearly demonstrated as a functional receptor in the lower urinary tract systems of human and other mammals. The $\alpha_{1L}$-subtype was also identified, if the intact segments of native tissues (e.g. human prostate). However, the $\alpha_{1L}$-subtype was not detected by a conventional binding experiment conducted with homogenized tissue. The fact that $\alpha_{1L}$-subtype is not detected in homogenized tissue means that purification of the $\alpha_{1L}$-subtype from tissue is very difficult. Unless the entity of the $\alpha_{1L}$-subtype is clarified, it will be very difficult to analyze the function of $\alpha_{1L}$-adrenergic receptor, in particular, to develop $\alpha_{1L}$-selective drugs (such as agonists or antagonists).

The inventors assumed that the $\alpha_{1L}$-subtype, whose entity is unknown, is constituted by binding of some sort of ancillary molecule to an already known subtype (probably, $\alpha_{1A}$-subtype). That is, the inventors assumed that the interaction between the subtype molecule and the molecule ancillary thereto, which constitute the $\alpha_{1L}$-subtype together, is dissolved by homogenizing tissue and, as a result, the $\alpha_{1L}$-subtype changes its properties into those of the $\alpha_{1A}$-subtype. In the result, the inventors found that the pharmacological profile of $\alpha_{1L}$-subtype was converted to that of $\alpha_{1A}$-subtype upon tissue homogenization. Furthermore, as a result of their diligent studies, the inventors confirmed that a particular protein binds to the $\alpha_{1A}$-subtype, and that coexpression of the protein with the $\alpha_{1A}$-subtype in a cultured cell leads to expression of a phenotype of $\alpha_{1L}$-subtype. That is, the inventors found that the $\alpha_{1L}$-subtype consists of a protein complex, identified a protein constituting the complex, and thereby accomplished the present invention.

In one embodiment, the present invention provides a protein complex that forms an $\alpha_{1L}$-subtype of adrenergic receptor. That is, a protein complex according to the present embodiment is an $\alpha_{1L}$-subtype of adrenergic receptor. The present embodiment makes it possible to provide treatment for any disease associated with an $\alpha_{1L}$-subtype whose entity has been clarified.

A polypeptide constituting the protein complex according to the present embodiment is already publicly known as a CRELD (cysteine-rich with EGF-like domains) 1α protein, whose missense mutation is pointed out as being associated with an atrioventricular septal defect (Gene 293: 47-57 (2002), *Am. J. Hum. Genet.* 72: 1047-1052 (2003)). Information on the sequence of the polypeptide is provided as NCBI Accession No. NM_015513 and, in the present specification, represented as SEQ ID NO: 1 (amino-acid sequence) and SEQ ID NO: 2 (nucleotide sequence). That is, the polypeptide constituting the protein complex according to the present embodiment may be a polypeptide consisting of an amino-acid sequence of SEQ ID NO: 1, or may be a polypeptide coded for by a polynucleotide consisting of a nucleotide sequence of SEQ ID NO: 2.

The polypeptide constituting the protein complex according to the present embodiment is not limited to a polypeptide consisting of an amino-acid sequence of SEQ ID NO: 1, and may be a mutant polypeptide retaining the activity of the original polypeptide. An example of such a mutant polypeptide is a polypeptide (i) consisting of an amino-acid sequence of SEQ ID NO: 1 with a deletion, insertion, substitution, or addition of one or several amino acids, and (ii) having the activity to form a complex with a GPCR and modify the ligand affinity of the GPCR.

With technical common sense in the field, a person skilled in the art could easily produce a mutant polypeptide, in the amino-acid sequence of a particular polypeptide with a deletion, insertion, substitution, or addition of one or several amino acids. Further, based on the descriptions in the present specification and the technical common sense, a person skilled in the art could easily confirm whether or not the mutant polypeptide retains the same activity as the original polypeptide.

Further, the polynucleotide encoding the polypeptide constituting the protein complex according to the present embodiment is not limited to a polynucleotide consisting of a nucleotide sequence of SEQ ID NO: 2, and only needs to be a mutant polynucleotide encoding a polypeptide retaining the activity to modify the ligand affinity of a GPCR with which the polypeptide has formed a complex. An example of such a mutant polynucleotide is, but is not limited to, (1) a polynucleotide consisting of a nucleotide sequence of SEQ ID NO: 2 with a deletion, insertion, substitution, or addition of one or several nucleotides, (2) a polynucleotide capable of hybridizing under stringent conditions with a polynucleotide consisting of a sequence complementary to a nucleotide sequence of SEQ ID NO: 2, or (3) a polynucleotide having a sequence identity of 70% or higher, preferably 80% or higher, or more preferably 85% or higher, with a polynucleotide consisting of a nucleotide sequence of SEQ ID NO: 2.

With technical common sense in the field, a person skilled in the art could easily produce: a mutant polypeptide, in the amino-acid sequence of a particular polynucleotide with a deletion, insertion, substitution, or addition of one or several amino acids; a mutant polynucleotide capable of hybridizing under stringent conditions with a particular polynucleotide; or a mutant polynucleotide having a sequence identity of 70% or higher with a particular polynucleotide. Further, based on the descriptions in the present specification and the technical common sense, a person skilled in the art could easily confirm whether or not a polypeptide coded for by the mutant polynucleotide retains the same activity as a polypeptide coded for by the original polynucleotide.

When used in the present specification, the term "stringent hybridization conditions" means overnight incubation at 42° C. in a hybridization solution (containing 50% formamide, 5×SSC [150 mM of NaCl, 15 mM of trisodium citrate], 50 mM of sodium phosphate (with a pH of 7.6), 5×Denhardt's solution, 10% dextran sulfate, and 20 µg/ml of sheared and denatured salmon sperm), followed by washing of a filter at approximately 65° C. in 0.1×SSC.

A specific procedure for hybridization only needs to be performed according to a method well known in the field (e.g., a method described in "*Molecular Cloning: A Laboratory Manual*, 3rd ed., J. Sambrook and D. W. Russell ed., Cold Spring Harbor Laboratory, NY (2001)" [which is incorporated by a reference to the present specification]).

The present invention thus far has been described by taking an adrenergic receptor as an example of a GPCR constituting a protein complex according to the present invention. However, a protein complex according to the present invention only needs to be a complex of a GPCR and (1) a polypeptide consisting of an amino-acid sequence of SEQ ID NO: 1; (2) a polypeptide (i) consisting of an amino-acid sequence of SEQ ID NO: 1 with a deletion, insertion, substitution, or addition of one or several amino acids, and (ii) having activity to modify ligand affinity of a GPCR with which the polypeptide has formed a complex; (3) a polypeptide encoded by a polynucleotide consisting of a nucleotide sequence of SEQ ID NO: 2; (4) a polypeptide (i) encoded by a polynucleotide consisting of a nucleotide sequence of SEQ ID NO: 2 with a deletion, insertion, substitution, or addition of one or several nucleotides, and (ii) having activity to modify ligand affinity of a GPCR with which the polypeptide has formed a complex; (5) a polypeptide (i) encoded by a polynucleotide capable of hybridizing under stringent conditions with a polynucleotide consisting of a sequence complementary to a nucleotide sequence of SEQ ID NO: 2 and (ii) having activity to modify ligand affinity of a GPCR with which the polypeptide has formed a complex; or (6) a polypeptide (i) coded for by a polynucleotide having a sequence identity of 70% or higher with a polynucleotide consisting of a nucleotide sequence of SEQ ID NO: 2 and (ii) having activity to modify ligand affinity of a GPCR with which the polypeptide has formed a complex. That is, the GPCR constituting the protein complex is not limited to an adrenergic receptor, but may be dopamine receptors, muscarinic receptors, or endothelin receptors. Further, a person skilled in the art could easily obtain, from a publicly-known database, information on the sequence of a GPCR constituting the present invention, and therefore could easily produce a desired protein complex, based on the descriptions in the present specification and the technical common sense.

[2. Lipid Membrane Containing a Protein Complex]

The present invention also provides a method for producing a protein complex of a GPCR and a particular polypeptide. The method according to the present invention for producing a protein complex is characterized by including the step of causing a GPCR and a particular polypeptide to coexist on a lipid membrane. That is, the present invention provides a lipid membrane containing a protein complex and a method for producing the same.

A lipid membrane according to the present invention is characterized by containing such a protein complex as described above. The lipid membrane according to the present invention may be a naturally-occurring lipid membrane, or may be an artificial lipid membrane. In cases where the lipid membrane is a naturally-occurring lipid membrane, the lipid membrane is intended to be a biological membrane. In cases where the lipid membrane is an artificial lipid membrane, the lipid membrane is intended to be a lipid planar membrane or liposome.

In one aspect of the present invention, a lipid membrane can be a biological membrane of transformant having introduced thereinto a polynucleotide encoding a polypeptide constituting a protein complex according to the present invention. Such a transformant can be obtained by introducing an expression vector containing the polynucleotide into a living organism so that the polypeptide is expressed in the form of a biological membrane. It should be noted that the living organism for use as the transformant may be a prokaryotic organism or a eucaryotic organism.

In another aspect of the present invention, a lipid membrane can be a lipid bilayer containing a polypeptide constituting a protein complex of the present invention. The lipid bilayer is a membranous structure composed of two layers of polar lipid (in particular, phospholipid). The lipid bilayer structure is stabilized as a two-dimensional structure when it takes the form of a sphere, but can be a planar structure if its end is isolated from a water molecule. When used in the present specification, the term "liposome" means a spherical lipid bilayer that is made artificially, and the term "lipid planar membrane" means a planar lipid bilayer that is made artificially. In the field, an artificial lipid bilayer is used in in vitro measurement of the activity of a membrane protein (e.g., a channel protein). In this way, a person skilled in the art could easily produce a lipid planar membrane and cause the lipid planar membrane to retain a protein (polypeptide) of interest. Further, liposome is a lipid artificial membrane that is referred to also as "vesicle", and can be produced by beating up a suspension of lipid (e.g., phospholipid) and then subjecting it to ultrasonication. In the field, researches have been widely conducted with liposome as a cell membrane model or as a means of drug delivery system (DDS). In this way, a person skilled in the art could easily produce liposome and cause the liposome to retain a protein (polypeptide) of interest.

In one embodiment, the present invention provides a lipid membrane containing an $\alpha_{1L}$-subtype of adrenergic receptor. As described above, the $\alpha_{1L}$-subtype of adrenergic receptor is a protein complex of an $\alpha_{1A}$-subtype molecule and a CRELD1α protein. The $\alpha_{1A}$-subtype of adrenergic receptor and the CRELD1α are both membrane-bound proteins, and, as described above, their interaction with each other is dissolved by homogenization (membrane disruption). That is, their interaction with each other is expressed by placing and retaining both of them on a lipid membrane.

In cases where the lipid membrane according to the present embodiment is a biological membrane, a method according to the present embodiment for producing a lipid membrane can also be a method for producing a transformant that expresses an $\alpha_{1L}$-subtype of adrenergic receptor, and only needs to include the step of coexpressing an $\alpha_{1A}$-adrenergic receptor protein and a CRELD1α protein. Information on the sequence of the $\alpha_{1A}$-subtype of adrenergic receptor is provided as NCBI Accession No. U03866 or NM_000680 and, in the present specification, represented as SEQ ID NO: 3 (amino-acid sequence) and SEQ ID NO: 4 (nucleotide sequence). That is, a method according to the present embodiment for producing a protein complex only needs to include the step of transforming a host with a vector containing a polynucleotide consisting of a nucleotide sequence of SEQ ID NO: 2 and a vector containing a polynucleotide consisting of a nucleotide sequence of SEQ ID NO: 4.

It is preferable that the vectors be each an expression vector having a polynucleotide of interest operably linked therewith. When used in the present specification, the term "operably linked" means that a polynucleotide encoding a peptide (or protein) of interest is under control of a control region such as a promoter and is in such a form that the peptide (or protein) can be expressed in a host. A procedure for establishing a desired vector by "operably linking" a polynucleotide encoding a peptide of interest with an expression vector is well known in the field. Further, a method for introducing an expression vector into a host is well known, too, in the field. Therefore, a person skilled in the art could easily generate a desired peptide in a host.

When used in the present specification, the term "transformant" means not only a cell, tissue, or an organ, but also an individual living organism. Examples of a living organism serving as an object of transformation include, but are not limited to, various microorganisms, plants, and animals. It should be noted that a transformant according to the present invention only needs to have introduced thereinto at least a polynucleotide encoding a polypeptide constituting a protein complex according to the present invention and express such polypeptides. That is, it should be noted that a transformant generated by means other than an expression vector is encompassed, too, in the technical scope of the present invention. Further, although it is preferable that a transformant according to the present invention be stably expressing a polypeptide constituting a protein complex according to the present invention, the polypeptide of interest may be transiently expressed.

It should be noted that use of a transformant coexistent with a protein complex according to the present embodiment makes it possible to screen an agonist for or antagonist against the complex by observing the behavior of a second messenger in a host cell.

In cases where the lipid membrane according to the present embodiment is an artificial membrane, the method according to the present embodiment for producing a lipid membrane can also be a method for producing a lipid planer membrane or liposome containing an $\alpha_{1L}$-subtype of adrenergic receptor and, more specifically, only needs to include the step of reconstituting an $\alpha_{1A}$-adrenergic receptor protein and a CRELD1α protein on an artificial planer membrane. With common sense in the field, a person skilled in the art could easily reconstitute a membrane protein on an artificial lipid membrane. Use of an artificial lipid membrane coexistent with a protein complex according to the present embodiment makes it possible to measure the ligand affinity of the complex.

[3. Use of a Lipid Membrane]

A person skilled in the art would easily understand that the above-described method for producing a lipid membrane can be both a method for producing a protein complex and a method for modifying the ligand affinity of a GPCR. That is, the present invention provides a method for modifying the affinity of a GPCR for its ligands.

Further, use of the lipid membrane according to the present invention makes it possible to screen an agonist for or antagonist against a GPCR having modified ligand affinity. That is, the present invention provides a method for screening agonists for or antagonists against a GPCR having modified ligand affinity.

The screening method according to the present invention is characterized by including the steps of generating such a protein complex as described above on a lipid membrane; and incubating the protein complex together with a candidate factor. When used in the present specification, "incubating" means causing a plurality of substances to coexist and putting them in such a state that they make sufficient contact with each other.

In a preferred embodiment, the screening method according to the present invention includes the step of incubating, together with a candidate factor, a transformant containing a GPCR of interest (e.g., a cell having $\alpha_{1L}$-subtype of adrenergic receptor expressed therein). The screening method according to the present embodiment makes it possible to screen agonists for or antagonists against a GPCR of interest (e.g., an $\alpha_{1L}$-subtype of adrenergic receptor) by measuring the fluctuation of a second messenger in a cell (e.g., the amount of cAMP in cases where the G protein is Gs protein or Gi protein or the concentrations of inosine triphosphate and $Ca^{2+}$ in cases where the G protein is Gq protein).

The agonists for $\alpha_{1L}$-subtype of adrenergic receptor can be used as a drug for urinary incontinence, a mydriatic drug, a drug for glaucoma, and a drug for central stimulation. The antagonists against $\alpha_{1L}$-subtype of adrenergic receptor can be used as a drug for urinary disturbance, a drug for Raynaud's disease, a drug for microcirculatory failure, an antihypertensive drug, a central depressant, a drug for improvement of renal blood flow, and a diuretic drug. Further, since $\beta_{1L}$-subtype of adrenergic receptor is known to be associated with heart disease and dopamine D2 receptor and muscarinic receptor are known to be associated with central nervous system disease, agonists or antagonists thereto are useful, too.

[4. Knockdown Cell and Use Thereof]

The present invention also provides a transformant in which a polypeptide that forms a protein complex with a GPCR has been knocked down and a method for producing the same. A method according to the present invention for producing a transformant is characterized by including the step of inhibiting expression of an endogenous polypeptide.

For example, the CRELD1α protein, which is a polypeptide that forms a complex with a GPCR, is expressed in various cells. Therefore, a transformant in which expression of an endogenous CRELD1α protein has been inhibited is very useful as a control cell that is used in analyzing the function of the protein complex or screening a target compound (e.g., an agonist or antagonist). The knockdown cell, described in this section, may be used alone, but is preferably used in combination with the above-described protein complex or the above-described lipid membrane containing the protein complex. It should be noted that the GPCR expressed in the object cell may be endogenous or exogenous.

In one aspect, the present invention can include the step of inhibiting expression of an endogenous CRELD1α protein in a cell in which a GPCR has been expressed. This makes it possible to modify the ligand affinity of the GPCR expressed in the cell. That is, the method according to the present invention for producing a transformant can be both a method for producing a transformant expressing a GPCR having modified ligand affinity and a method for modifying the affinity of a GPCR for its ligand. In one embodiment, the present invention can include the step of inhibiting expression of an endogenous CRELD1α protein in a cell expressing an $\alpha_{1L}$-subtype of adrenergic receptor. This makes it possible to modify a cell indicative of a phenotype of $\alpha_{1L}$-subtype to be a cell indicative of a phenotype of $\alpha_{1A}$-subtype.

It is preferable that an RNAi method be used as a technique for inhibiting expression of an endogenous CRELD1α protein. The RNAi method is a technique well known in the field; for example, expression of an endogenous CRELD1α protein can be successfully inhibited by introducing, into a cell of interest, an oligonucleotide consisting of a nucleotide sequence of SEQ ID NO: 5. In the case of use of a vector for introducing, into a cell of interest, an oligonucleotide consisting of a nucleotide sequence of SEQ ID NO: 5, it is preferable that an oligonucleotide consisting of a nucleotide sequence of SEQ ID NO: 6 be used as an antisense, without implying any limitation.

The present invention further provides a method, characterized by using the above-described transformant, for screening an agonist for or antagonist against a GPCR having modified ligand affinity.

The present invention is not limited to the description of the embodiments above, but may be altered by a skilled person within the scope of the claims. An embodiment based on a proper combination of technical means disclosed in different embodiments is encompassed in the technical scope of the present invention.

All the academic and patent literatures cited herein are incorporated by references to the present specification.

EXAMPLE

[1. Structures]

A human $\alpha_{1A}$-adrenergic receptor gene (ADRA1A) was cloned from a human prostate library with a PCR technique. The cloned gene had a whole length of 1465 bp, and had an ORF sequence perfectly matching that of the human alpha-1A gene (NCBI Accession No. U03866 or NM_000680), which has conventionally been reported. Further, sequences preceding and following the ORF sequence matched those reported in Hirasawa et al. (1993).

A CRELD1α gene was cloned from a human prostate cDNA library. As a result of sequence determination, the cloned gene matched that reported in Rupp et al. (2002) (NCBI Accession No. NM_015513).

Next, the coding region of the ADRA1A gene was subcloned into the EcoRI restriction enzyme site of the multi-cloning site A of the pIRES (Clonetech, Catalog No. PT3266-5). Further, the coding region of the CRELD1α was subcloned into the XbaI restriction enzyme site of the multi-cloning site B of the pIRES. For the purpose of subcloning, each of the genes had a restriction enzyme adapter added to each end.

[2. Production of a Transformant]

The vector was amplified/purified in a conventional method, and then transfected into CHO-K1 cells, which are cells of Chinese Hamster ovarian origin, with Lipofectamine 2000 (Invitrogen Corporation) according to the manufacturer's protocol. Two days after the transfection, 1200 µg/ml of the antibiotic Geneticin (G418) were added to the DMEM culture medium. Cells into which the vector had not been transfected, i.e., cells subjected to the same operation with Lipofectamine 2000 and the like expect that the vector had not been added, were completely annihilated at a G418 concentration of 1000 µg/ml. The G418-resistant cells were diluted, suspended, and injected dividedly into a 96-well plate so that an average of 0.5 cells was put in per well, and a single colony was chosen. This operation was repeated three times, whereby a stable clone (αL cells) having coexpressed the ADRA1A gene and the CREDL1α gene was produced. Further, as control groups, the cells ($\alpha_{1A}$ cells) having stably expressed only the ADRA1A gene and the cells (CREDL1α cells) having stably expressed only the CREDL1α gene were produced.

[3. Binding Experiment]

The drugs used in the binding experiment and their proper chemical names are as follows: silodosin, prazosin, tamsulosin, RS-17053 (N-[2-(2-cyclopropylmethoxyphenoxy) ethyl]-5-chloro-α,α-dimethyl-1H-indole-3-ethanamine hydrochloride), BMY 7378 (8-[2-[4-(2-methoxyphenyl)-1-piperazinyl]ethyl]8-azaspiro[4,5]decane7,9-dione dihydrochloride).

The stable clone was studied by a pharmacological binding method with [$^3$H]-silodosin, which is a radioligand. An experiment was conducted using a whole-cell binding method. That is, cells were scattered two to three days before the experiment so that they are semi-confluent, washed twice with ice-cold PBS, and then scraped by a scraper. The cells thus collected were suspended again in a Krebs-HEPES solution, and then incubated at 4° C. for four hours together with [$^3$H]-silodosin and another drug as needed. Thereafter, the cells were filtered/washed by a Whatmann GC/F filter pretreated with polyethylene imine, and the radioactivity was measured by a liquid scintillation counter. The non-specific binding was evaluated as binding in the presence of 30 µM phenotolamine.

[A] Saturation Binding Experiment According to the Whole-Cell Method

Figure 1:
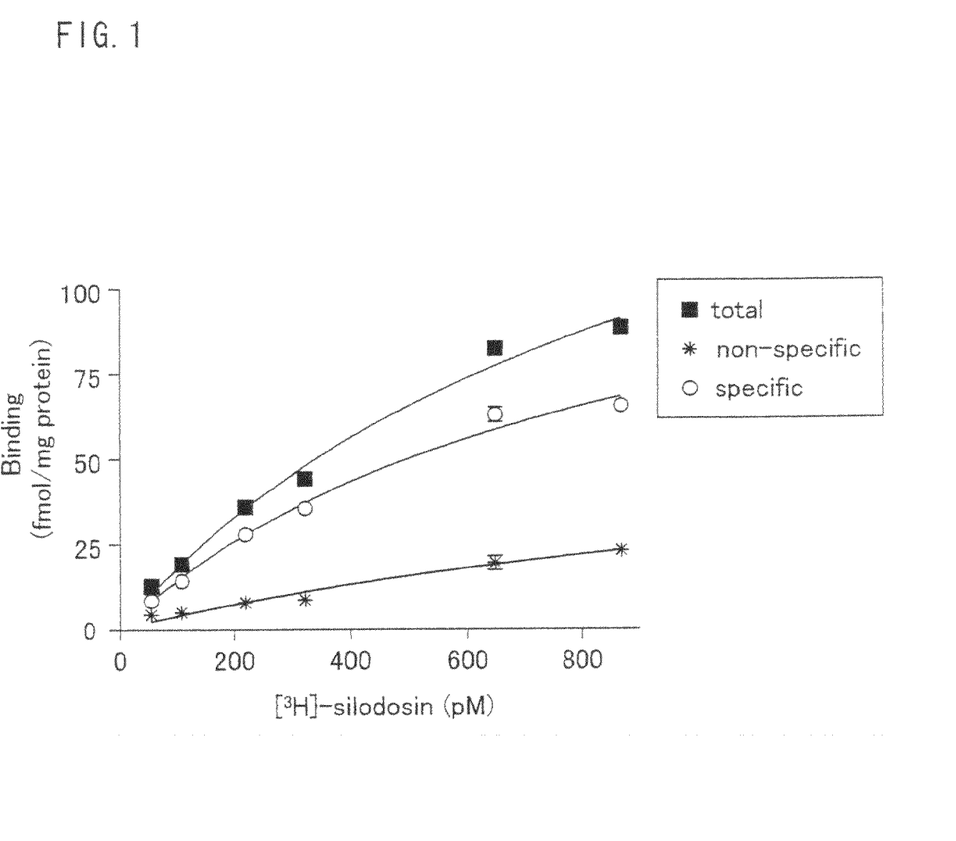
FIG. 1 shows saturation binding curves for [$^3$H]-silodosin in $α_{1L}$ cells (whole cell binding experiment).

The binding of [$^3$H]-silodosin of various concentrations (30 to 1000 pM) to the $\alpha_{1L}$ cells was examined (FIG. 1). FIG. 1 shows a saturation binding curve obtained by the whole-cell method. The specific binding of [$^3$H]-silodosin to the $\alpha_{1L}$ cells exhibited a maximum binding amount (Bmax) of 134 fmol/mg protein and a Kd value of 843 pM (pK$_D$=9.1).

[B] Competitive Binding Experiment

Silodosin is known to bind selectively to the $\alpha_{1A}$- and $\alpha_{1L}$-subtypes with a high affinity. The term "high affinity" here means a Kd value of 1 nM or less. In order to identify the pharmacologic properties of receptors expressed in the $\alpha_{1L}$ cells, a competitive binding experiments with prazosin at 300 pM [$^3$H]-silodosin binding sites were conducted using the whole-cell binding experiment method. The $\alpha_{1A}$ cells were used as control cell line. [$^3$H]-silodosin is known as a selective antagonist of $\alpha_{1A}$- and $\alpha_{1L}$-subtypes both.

Figure 2:
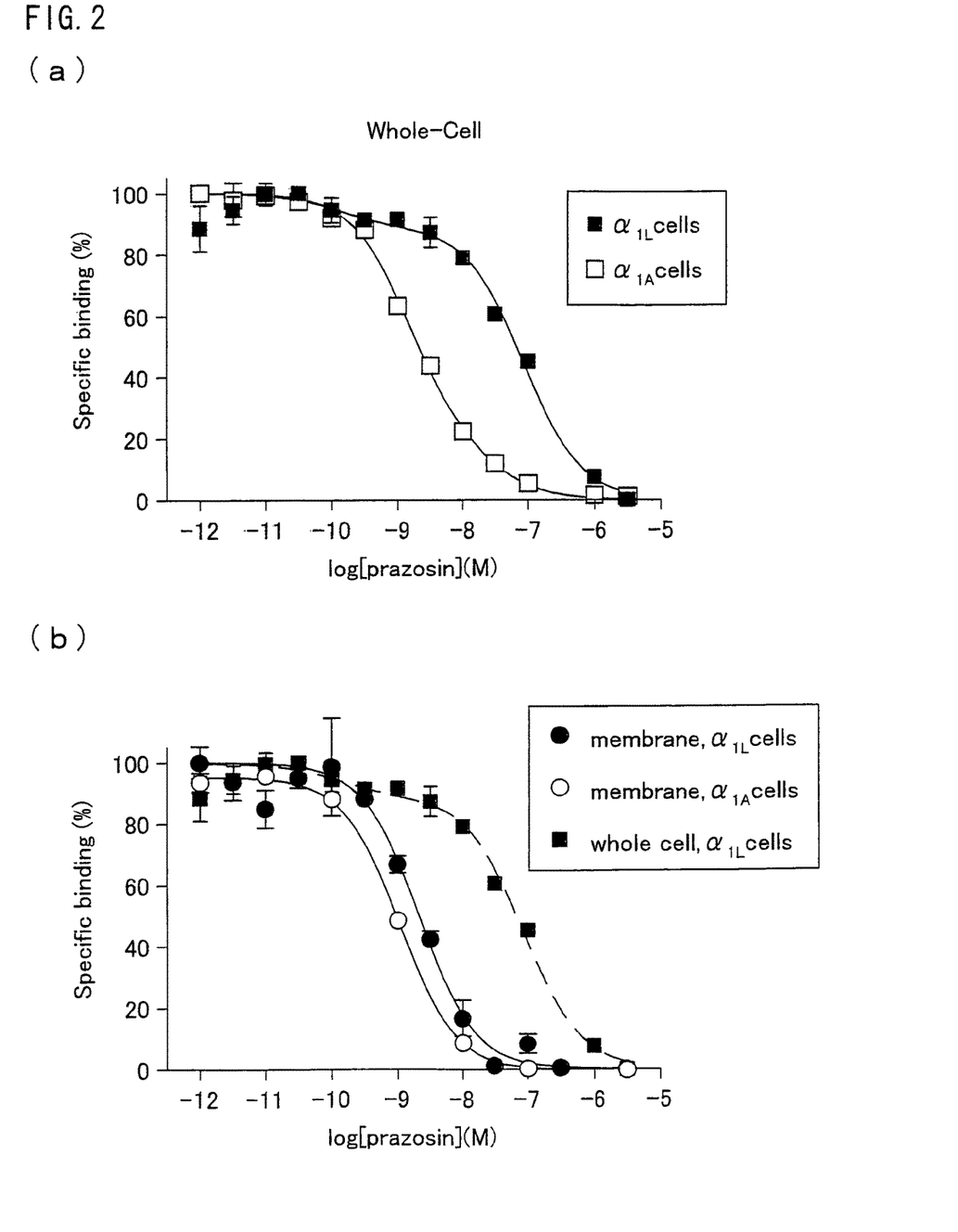

As shown by the competitive curve in (a) of FIG. 2, most (88% or higher) of receptors in the $\alpha_{1L}$ cells exhibit low sensitivity to prazosin (pK$_i$=7.6). Further, the receptors are similarly low in sensitivity to RS-17053, and have high sensitivity to tamsulosin. Further, the receptors in the $\alpha_{1L}$ cells exhibit only low sensitivity to BMY 7378 (Table 2). On the other hand, the sensitivities (pK$_i$ values) of the $\alpha_{1A}$ cells, which were used as a control group, to prazosin (FIG. 2), tamsulosin, and RS-17053 are as high as 9.5, 9.9, and 8.8, respectively, which correspond to the $\alpha_{1A}$ properties hitherto reported (Table 2).

TABLE 2

Pharmacologic Properties of $\alpha_{1L}$-adrenergic Receptors in Two Cell Lines and Human Prostate

| Drug | $\alpha_{1L}$ Cells | $\alpha_{1A}$ Cells | Human Prostate |
|---|---|---|---|
| [$^3$H]-silodosin (pK$_D$) | 9.1 | 9.7 | 9.5 |
| Prazosin | 7.6 | 9.5 | 8.3 |
| Tamsulosin | 9.3 | 9.9 | 10.0 |
| RS-17053 | <6.0 | 8.8 | 6.6 |
| BMY 7378 | <6.0 | 6.5 | 5.9 |

In this table, the inhibition constants (K$_i$) of competitive drugs at [$^3$H]-silodosin binding sites in the $\alpha_{1L}$ cells, the $\alpha_{1A}$ cells, and the human prostate tissue segments are shown as $-\log K_i$ (pK$_i$). However, the value of [$^3$H]-silodosin exhibits a pK$_D$ value (dissociation equilibrium constant) calculated from the saturation binding curve. The value is an average of three to four examples.

Further, (b) of FIG. 2 shows results obtained by examining sensitivity to prazosin in the homogenates of $\alpha_{1L}$ cells and the homogenates of $\alpha_{1A}$ cells. In the homogenates, the $\alpha_{1L}$ cells exhibited as high sensitivity to prazosin as the $\alpha_{1A}$ cells. This fact coincides well with the results that the $\alpha_{1L}$ receptors in prostate and brain disappeared upon tissue homogenization and, that the pharmacological profile was converted to $\alpha_{1A}$ phenotype.

Binding affinities for various drugs of $\alpha_1$-adrenergic receptors in $\alpha_{1L}$ and $\alpha_{1A}$ cells and human prostate are summarized in Table 2. The $\alpha_{1L}$ cells, in which the ADRA1A gene and the CRELD1α gene were coexpressed, differ in receptor properties from $\alpha_{1A}$ receptors, and coincides well in pharmacologic properties with $\alpha_{1L}$ receptors reported in human prostates and the like. Therefore, unlike the $\alpha_{1A}$ cells, the $\alpha_{1L}$ cells are considered as a cell line having expressed $\alpha_{1L}$ receptors predominantly.

[4. Intracellular Ca$^{2+}$ Measurement Experiment]

Furthermore, in order to completely get rid of the influence of CRELD1α, which might have been endogenously expressed in the $\alpha_{1A}$ cells, the RNAi method was used to produce cells in which CRELD1α expression had been knocked down (such cells being hereinafter referred to as "KD cells". In order to inhibit gene expression with the RNAi method, a vector was produced by inserting an oligonucleotide (sense sequence; GATCCAGGCGACTTAGTGTT-CACCTTCAAGAGAGGTGAACACTAAGTCGCCTTTA: SEQ ID NO: 5, antisense sequence; AGCTTAAAGGCGAC-TTAGTGTTCACCTCTCTTGAAGGTGAACACTAAGT-CGCCTG: SEQ ID NO: 6) containing a coding region of mRNA of chinese hamster CRELD1α into a commercially-available pSilencer™ 4.1-CMV hygro (Ambion, Inc.)

according to the instruction manual therefor, and then transfected into the $\alpha_{1A}$ cells in the same procedure as described above. The $Ca^{2+}$ response to noradrenaline in the KD cells was examined according to a fluorescent photometric method with Fura-2, which is a fluorescent dye. The $pEC_{50}$ value of the $Ca^{2+}$ response to noradrenaline in the KD cells was 7.9. On the other hand, when the cells were treated in advance with prazosin $10^{-8}$ M for two minutes, the dose-response curve of $Ca^{2+}$ response to noradrenaline shifted rightward, and the $pK_B$ value of prazosin was calculated to be 9.3. This shows that the $Ca^{2+}$ response to noradrenaline in the KD cells coincides with the properties of the $\alpha_{1A}$-subtype.

Thus, when the expression of endogenous CRELD1α in a CHO cell having a gene of $\alpha_{1A}$-subtype expressed therein was inhibited by the RNAi method, $\alpha_{1A}$ receptor properties were perfectly exhibited. It should be noted that there have been some experiments where the receptor functions, such as $Ca^{2+}$ response, of $\alpha_{1A}$-subtype were examined by using CHO cells in which a gene of the receptor had been expressed. However, there has not necessarily been an agreement in the receptor properties obtained as a result of those experiments.

Use of the present invention makes it possible to clarify a GPCR whose entity has been unknown and thereby provide treatment for any disease associated with the receptor, and also makes it possible to modify the ligand affinity of a GPCR.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

It is now clear that $\alpha_{1L}$-AR is a functional receptor and a main target for therapeutic drugs in lower urinary tract system. Thus, the present $\alpha_{1L}$-AR expression cells, developed by the inventors, should be considered to be extremely useful in drug development for urinary disturbance in patients with benign prostatic hyperplasia and for urinary incontinence. Further, the $\alpha_{1L}$-AR expression cells are considered to be extremely useful as a method for screening therapeutic drugs for any disease associated with $\alpha_{1L}$-AR.

What is claimed is:

1. A method for modifying ligand affinity of a $GPCR\alpha_{1A}$, the method comprising the steps of:
   (a) providing a cell; and
   (b) coexpressing both a $GPCR\alpha_{1A}$ and a polypeptide in the cell;
   (c) measuring ligand affinity of the $GPCR\alpha_{1A}$ in the cell which expresses both the $GPCR\alpha_{1A}$ and the polypeptide, and in a cell which expresses the $GPCR\alpha_{1A}$ and does not express the polypeptide; and
   (d) comparing a result obtained from the cell which expresses both the $GPCR\alpha_{1A}$ and the polypeptide, with a result obtained from the cell which expresses the $GPCR\alpha_{1A}$ and does not express the polypeptide,
   the polypeptide being:
   (i) a polypeptide consisting of an amino acid sequence of SEQ ID NO: 1; or
   (ii) a polypeptide encoded by a polynucleotide consisting of a nucleotide sequence of SEQ ID NO: 2;
   wherein $GPCR\alpha_{1A}$ affinity increases or decreases in the presence of the polypeptide.

2. A method for screening an agonist for or antagonist against a $GPCR\alpha_{1L}$, the method comprising the steps of:
   (a) providing a cell;
   (b) coexpressing both a $GPCR\alpha_{1A}$ and a polypeptide in the cell to form a $GPCR\alpha_{1L}$; and
   (c) incubating the cell expressing the $GPCR\alpha_{1L}$ together with a candidate factor,
   the method further comprising the steps of:
   (d) measuring an intracellular $Ca^{2+}$ concentration or metabolism of intracellular inositol phosphate in the cell expressing the $GPCR\alpha_{1L}$ before or after the incubating step; and
   (e) determining the candidate factor as to whether the candidate factor is an agonist for or antagonist against the $GPCR\alpha_{1L}$, wherein
   (i) the candidate factor is determined as an agonist for the $GPCR\alpha_{1L}$, when the value obtained by the measuring conducted after the incubating step is increased compared to the value obtained by the measuring conducted before the incubating step, and
   (ii) the candidate factor is determined as an antagonist against the $GPCR\alpha_{1L}$, when the value obtained by the measuring conducted after the incubating step is not altered compared to the value obtained by the measuring conducted before the incubating step; wherein the measuring conducted after the incubating step is carried out in the presence of an agonist for the $GPCR\alpha_{1L}$,
   the polypeptide being:
   (i) a polypeptide consisting of an amino acid sequence of SEQ ID NO: 1; or
   (ii) a polypeptide encoded by a polynucleotide consisting of a nucleotide sequence of SEQ ID NO: 2.

3. The method as set forth in claim 1, wherein $GPCR\alpha_{1A}$ affinity increases in the presence of the polypeptide.

4. The method as set forth in claim 1, wherein $GPCR\alpha_{1A}$ affinity decreases in the presence of the polypeptide.

* * * * *